United States Patent [19]

Anderson-Shanklin

[11] 4,232,687

[45] Nov. 11, 1980

[54] APPARATUS AND METHOD FOR DETERMINING NEWBORN INFANT FEEDING CAPABILITY

[75] Inventor: Gene C. Anderson-Shanklin, Oak Park, Ill.

[73] Assignee: University of Illinois Foundation, Urbana, Ill.

[21] Appl. No.: 829,623

[22] Filed: Sep. 1, 1977

[51] Int. Cl.³ .......................... A61B 5/00; A61B 5/10
[52] U.S. Cl. ...................................... 128/777; 73/731
[58] Field of Search ............... 128/2 S, 2 R, 252, 359, 128/360, 341, 208, 281, 2.05 E; 73/379, 714, 715, 731; 119/14.14; 35/29 E, 22 R

[56] References Cited

U.S. PATENT DOCUMENTS

| | | | |
|---|---|---|---|
| 3,417,743 | 12/1968 | Carrera | 128/2 S |
| 3,480,003 | 11/1969 | Crites | 128/2 S |
| 3,589,194 | 6/1971 | Noorlander | 73/389 |
| 3,827,433 | 8/1974 | Shannon | 128/145.5 |
| 3,895,533 | 7/1975 | Steier | 73/409 |
| 4,112,596 | 12/1978 | Fletcher | 35/35 R |

OTHER PUBLICATIONS

Sameroff, "An Apparatus for Recording Sucking and Controlling Feeding," Psychon. Sci., vol. 2, pp. 355–356, 1965.
Dubignon et al., "Sucking in the Newborn During a Feed," Journal of Experimental Child Psychology, pp. 282–298, 1969.
Kron et al., "Method of Measuring Sucking Behavior in Newborn Infants," Psychosomatic Medicine, vol. XXV, #2, 181–191, 1963.
Kron et al., "Newborn Sucking Behavior Affected by Obstetric Sedation," Pediatrics, vol. 37, pp. 1012–1016, 1966.

Primary Examiner—Robert W. Michell
Assistant Examiner—Jeffrey W. Tayon
Attorney, Agent, or Firm—Martin Novack

[57] ABSTRACT

The disclosure is directed to a method and apparatus for determining a newborn infant's capability to orally accept nourishment. In accordance with the method of the invention, a test nipple is inserted in the mouth of an infant. Further method steps comprise measuring the suction which the infant applies to the test nipple, and measuring the expression force which the infant applies to the test nipple. The infant's capability of orally accepting nourishment is then determined as a function of the measured suction and expression. In accordance with the apparatus of the invention, there is provided a test nipple, and first and second transducers adapted for coupling to the test nipple. The first transducer is operative to generate a suction-indicative electrical signal, and the second transducer is operative to generate an expression-indicative electrical signal. A timing circuit is provided for defining successive time intervals. A circuit is provided for detecting and storing the peak value of the suction-indicative electrical signal which occurs during each of the successive time intervals and for detecting and storing the peak value of the expression-indicative electrical signal which occurs during each successive time interval. The determined peak suction-indicative and expression-indicative signal values are recorded.

5 Claims, 3 Drawing Figures

APPARATUS AND METHOD FOR DETERMINING NEWBORN INFANT FEEDING CAPABILITY

The invention described herein was made in the course of work under a grant or award from the Department of Health, Education and Welfare.

BACKGROUND OF THE INVENTION

This invention relates to clinical techniques for the infant nursery and, more particularly, to a method and apparatus for determining an infant's capability to orally take nourishment by sucking.

An important determination that must be made for newborn infants, and especially premature newborns, is the capability of the infant to accept liquid nourishment orally from a nipple. An infant who has insufficient capability to receive nourishment orally, and who is given a feeding bottle before this capability develops, is in danger of regurgitation and aspiration, events which could lead to "milk aspiration" pneumonia and death. Accordingly, doctors and nurses tend to be relatively conservative in appraising the infant's capability to take nourishment orally. Initial feedings of low-risk newborns are commonly delayed for 12 hours or more and occasionally for 24 hours or more. High-risk infants are commonly fed by routes which circumvent the need to suck and swallow. Such routes include intravenous, nasogastric, or nasojejunal infusion. These feeding modes are not without complication and are also recognized to be less adequate than sucking milk from a nipple, but the claim is they are safer. Also, applicant has noted that the absence of normal feeding can have a degenerative effect since the infant who is fed intravenously or by tube has little opportunity to develop the muscles and coordination needed to improve sucking and swallowing capabilities.

The determination of the infant's ability to accept nourishment orally is generally made on the basis of a relatively large number of inputs pertaining to the infant's overall condition. Since there are no systematic criteria for such determinations, a degree of guesswork is typically employed and there is little confidence that a correct decision has been made.

It is an object of the present invention to provide an improved and consistent technique for determination of a newborn infant's ability to take oral nourishment safely.

SUMMARY OF THE INVENTION

Applicant has discovered that an infant's ability to take oral nourishment can be directly correlated with the intensity of the infant's sucking and expression levels on a test nipple and, in particular, the peaks of the infant's sucking and expression levels during each of the series of successive time intervals.

The invention is a method and apparatus for determining a newborn infant's capability to orally accept nourishment. In accordance with the method of the invention, a test nipple is inserted in the mouth of an infant. Further method steps comprise measuring the suction which the infant applies to the test nipple, and measuring the expression force which the infant applies to the test nipple. The infant's capability of orally accepting nourishment is then determined as a function of the measured suction and expression. In the preferred form of the method of the invention, the step of measuring suction comprises measuring the peak suction within a prescribed time interval and the step of measuring the expression comprises measuring the peak expression within a prescribed time interval. The method is repeated for a successive series of time intervals, and the peak values of both sucking and expression are recorded for later examination.

Measurements of infant sucking (negative pressure applied to tip of nipple) and expression (squeezing pressure applied to nipple) have been performed in the prior art for various purposes. To applicant's knowledge, prior art studies were always made after oral feedings had been initiated, i.e., more than about twelve hours after birth. In such studies, infant sucking behavior has been examined for its relationship, inter alia, to maternal medications, respiratory rates, swallowing, infant body tension, infant age, etc. However, there has been no suggestion that sucking behavior prior to oral feedings and during the first few hours of life could be used to determine the ability of the newborn to take oral nourishment safely earlier.

In accordance with the apparatus of the invention, there is provided a test nipple, and first and second transducer means adapted for coupling to the test nipple. The first transducer means is operative to generate a suction-indicative electrical signal, and the second transducer means is operative to generate an expression-indicative electrical signal. Timing means are provided for defining successive time intervals of predetermined duration. Means are provided for detecting and storing the peak value of the suction-indicative electrical signal which occurs during each of the successive time intervals and for detecting and storing the peak value of the expression-indicative electrical signal which occurs during each successive time interval. Finally, means are provided for recording the determined peak suction-indicative and expression-indicative signal values. In the preferred embodiment of the apparatus of the invention, analog-to-digital converter means are provided for converting the suction-indicative and expression-indicative signals to digital form before the recording thereof. In this embodiment, means are provided for displaying the peak suction-indicative and expression-indicative values. The peak values are also printed out for examination by medical personnel to determine the infant's capability to accept oral nourishment safely.

Apparatus for measuring sucking and/or expression parameters exist in the prior art. Kron et al. (*Psychosomatic Medicine*, 25, 181, 1963) measured the sucking behavior of infants. The apparatus provided control over the flow of nutrients and allowed recording of a graph of continuous sucking pressures. Sucking components are disclosed as being measured and recorded on a polygraph by Dubignon et al. (*Journal of Experimental Child Psychology*, 7, 282-29, 1969). A further system wherein sucking and expression components are measured and recorded on a polygraph is disclosed by Sameroff (*Psychonomic Science*, 2, 1965). In the listed references, at least a portion of the testing involves nutrients to be received by the infant, and there is no suggestion that the peaks of suction and expression recorded during successive time intervals can be measured, stored, and used to make decisions regarding the ability to take oral nourishment safely in the first place.

A further concern of applicant is that sucking and swallowing, the customary means by which newborns take nourishment, may be essential to optimal completion of the gastrointestinal cycle (e.g., to mixing the nutriment with digestive secretions, to absorbing nutrients, and to excreting waste products). Certain intrusive procedures, such as starting an intravenous infusion, can be avoided if oral feedings can begin early. This is important since these measures cause crying behavior which is exhausting to the infant and further compromises the infant's ability to take oral nourishment safely. The invented technique provides solution to this problem, since it demonstrates that certain suction and expression pressures are related to safe oral feeding and that these same pressures are present during the first hour of life in almost all full-term infants, and during the first three to six hours of life in many low-birth-weight infants.

Further features and advantages of the invention will become more readily apparent from the following detailed description when taken in conjunction with the accompanying drawing.

DESCRIPTION OF THE PREFERRED EMBODIMENT

Figure 1:
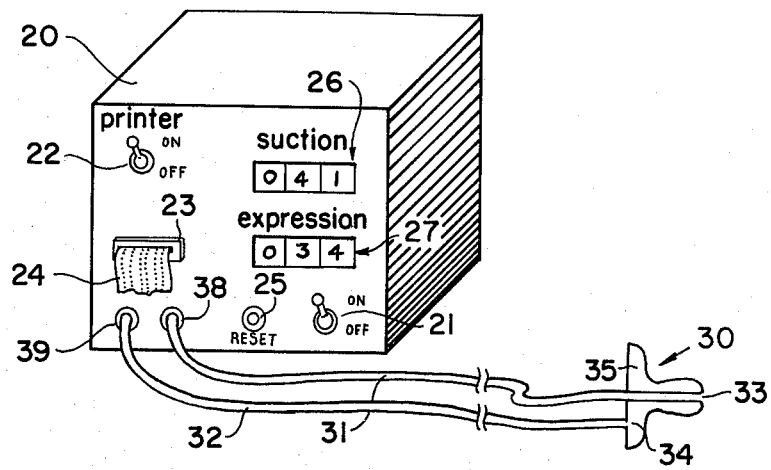
FIG. 1 is an elevational perspective view of an apparatus in accordance with an embodiment of the invention.

Referring to FIG. 1, there is shown an external perspective view of an apparatus in accordance with an embodiment of the invention. A console 20, which houses the electronics, controls, displays, and transducers, has a silastic plastic test nipple 30 coupled thereto via flexible silastic plastic tubes 31 and 32. The tubes are coupled to connectors 38 and 39, respectively, on the face of console 20, and the connectors are, in turn, coupled to transducers within the console. The face of console 20 also includes a power on-off switch 21, a printer on-off switch 22, a slot 23 from which a tear-off printed paper tape 24 is released, a reset button 25, and two three-digit displays 26 and 27.

Figure 2:
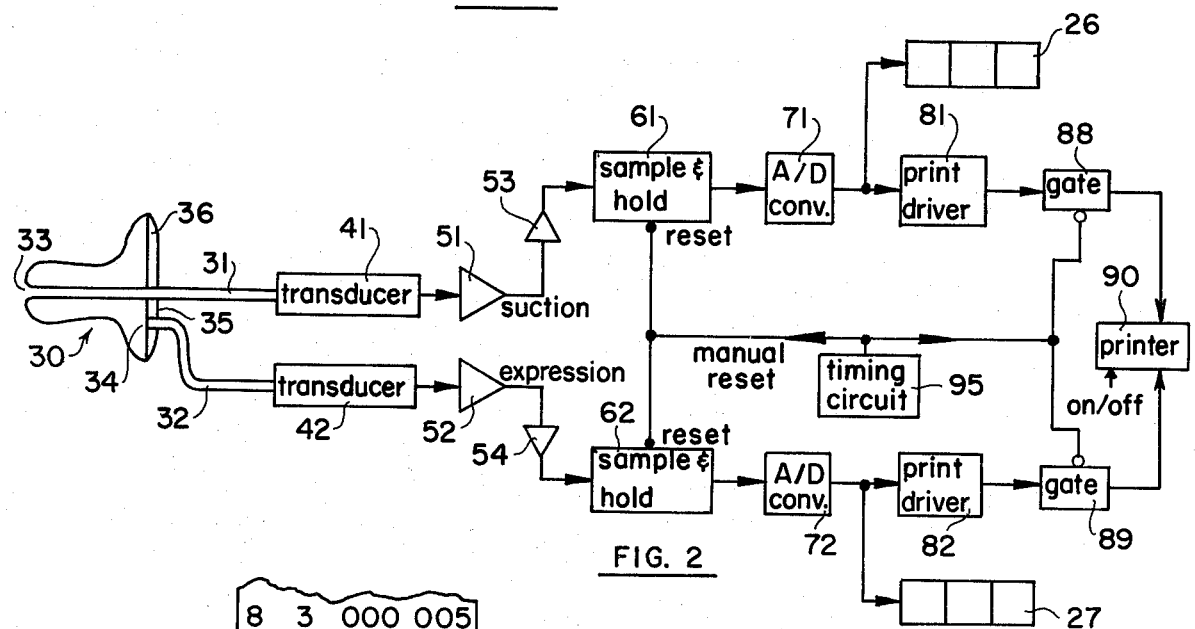
FIG. 2 is a block diagram of the apparatus of the FIG. 1 embodiment.

FIG. 2 is a block diagram of the apparatus of FIG. 1. The test nipple 30 has a flexible tube 31 coupled to the opening 33 at the tip of the nipple 30. The other flexible tube 32 is coupled to an opening 34 which, in the present embodiment, is in the base 35 of nipple 30, but could be in any suitable place in the nipple body. The open sawed-off base 35 of the nipple 30 is sealed against a plastic disc 36. Tubes 31 and 32 pass through two holes in this disc. Any slight space between the disc and the tubes is sealed with a silastic sealer. The other ends of tubes 31 and 32 are respectively coupled to pressure transducers 41 and 42, these transducers each generating an electrical output signal whose magnitude is related to the pressure in its associated tube. Accordingly, and as is known in the art, a negative pressure applied to the tip of the nipple 30 by an infant's sucking action will result in an output of transducer 41 which relates to the sucking pressure. Also, squeezing on the nipple by the infant's lips, gums, tongue, and/or palate will cause a positive pressure, designated as "expression", which results in an output of transducer 42 that is related to the magnitude of the infant's applied expression force. The outputs of transducers 41 and 42 are respectively coupled, via amplifiers 51 and 52 and filters 53 and 54, to sample and hold circuits 61 and 62. The circuits 61 and 62 may be any suitable circuits for detecting and storing the peak value of its input signal until reset by a signal at its reset terminal, whereupon it repeats its function. For example, the circuits 61 and 62 may comprise field effect transistor (FET) peak detector circuits which include a capacitor that tracks and holds the maximum input voltage until a reset signal is received whereupon the capacitor is discharged and will begin anew to detect and store the peak voltage which occurs during the next defined time interval.

The outputs of peak detectors 61 and 62 are coupled to analog-to-digital (A/D) converters 71 and 72 which convert the held peak signals to digital form. The outputs of A/D converters 71 and 72 are respectively coupled to the digital displays 26 and 27 which are on the front of console 20 of FIG. 1. The outputs of the A/D converters 71 and 72 are also respectively coupled to printing driver units 81 and 82 whose outputs are, in turn, coupled to the inputs of the gates 88 and 89, respectively. A timing circuit 95 generates a timing signal being coupled to the reset terminals of the units 61 and 62 and the enable terminals of the gates 88 and 89. When the timing signal occurs, the outputs of gates 88 and 89 drive a printer 90 to print, in two separate columns, numbers representative of the values held by the units 61 and 62 at the end of each time interval of predetermined duration; i.e., at the end of each fifteen second interval in this embodiment.

Figure 3:
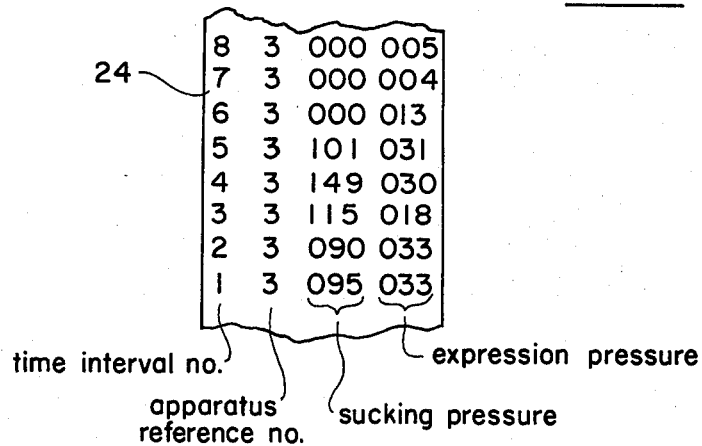
FIG. 3 illustrates a portion of output tape from the printer of the apparatus of FIG. 1.

In operation, the pressures caused by an infant's sucking and expression on the nipple 30 will cause outputs of the transducers 41 and 42, respectively. Operation of sample and hold circuits 61 and 62 results in display of the peak values of sucking and expression on the displays 26 and 27, respectively, of console 20. Each display will, of course, indicate only the peak values and will remain the same, during a particular fifteen second interval, until the infant exerts a sucking or expression pressure that exceeds a previous maximum for that particular interval whereupon the display will reflect the new maximum. After each interval of fifteen seconds, the circuits 61 and 62 are reset and again begin detection of maxima for the particular time interval. The printer 90 will print out the values for sucking and expression on paper tape 24, such as is shown in FIG. 3. The leftmost column indicates the time interval reference number. The next column indicates which apparatus has been used. The next and rightmost columns respectively indicate the peak values of sucking and expression, in mm of Hg, for each interval.

Applicant has found that peak sucking scores above about 100 mm Hg and peak expression scores above about 40 mm Hg indicate that it is safe to feed. Stability of the sucking and expression scores, however, should also be observed and is believed to be important in establishing, with a high degree of confidence, that an infant can safely receive oral nourishment.

The disclosed apparatus and method can also be utilized for assessment and screening for general condition and prognosis, since sucking response appears to be in part a function of condition. For example, the sucking response is found to decrease sharply at levels of serum indirect bilirubin as low as 7 mg%. This indicates these low levels of serum indirect bilirubin may have a heretofore unsuspected cerebral effect, a finding which has significant implications for management of newborn infants.

I claim:

1. Apparatus for recording parameters which are determinative of an infant's capability of taking oral nourishment safely, comprising:
   a test nipple;
   first and second transducer means adapted for coupling to said nipple, said first transducer means being operative to generate a suction-indicative electrical signal and said second transducer means being operative to generate an expression-indicative electrical signal;
   timing means for defining successive time intervals of predetermined duration;
   means coupled to said first transducer means and to said timing means for detecting and storing the peak value of said suction-indicative signal which occurs during each of said successive time intervals;
   means coupled to said second transducer means and to said timing means for detecting and storing the peak value of said expression-indicative signal which occurs during each of said successive time intervals; and
   means for displaying the stored peak suction-indicative and expression-indicative signal values.

2. Apparatus as defined by claim 1 further comprising analog-to-digital converter means for converting the suction-indicative and expression-indicative signals to digital form before the recording thereof.

3. Apparatus as defined by claim 1 further comprising means for continuously displaying the peak suction-indicative and expression-indicative values.

4. Apparatus as defined by claim 1 further comprising means for recording the stored suction-indicative and expression-indicative signals.

5. Apparatus as defined by claim 1 wherein said means for determining the peak suction-indicative and expression-indicative signals comprises first and second sample and hold circuits respectively coupled to said first and second transducers.

* * * * *